United States Patent [19]

Borchert et al.

[11] 3,945,941
[45] Mar. 23, 1976

[54] HAZARD REDUCTION FOR BULK SHIPMENT QUANTITIES OF AQUEOUS TERTIARY BUTYL HYDROPEROXIDE

[75] Inventors: Alfred E. Borchert, Cherry Hill, N.J.; Eugene C. Capaldi, Broomall, Pa.; Donnell A. Ballard, Princeton, N.J.

[73] Assignee: Oxirane Corporation, Princeton, N.J.

[22] Filed: Jan. 7, 1975

[21] Appl. No.: 539,196

Related U.S. Application Data

[63] Continuation-in-part of Ser. No. 347,967, April 4, 1973, abandoned.

[52] U.S. Cl. ............... 252/186; 53/6; 106/15 FP; 206/84; 252/8.1; 252/399; 252/407; 260/610 A; 260/DIG. 24
[51] Int. Cl.$^2$ A62C 3/12; B65D 8/24; C07C 179/02
[58] Field of Search ............ 252/186, 8.1, 399, 407; 106/15 FP; 206/84, 260/610A, DIG. 24; 53/5, 6

[56] References Cited
UNITED STATES PATENTS

| | | | |
|---|---|---|---|
| 3,063,559 | 11/1962 | Bergman | 206/84 |
| 3,377,766 | 4/1968 | Nelson | 206/84 |
| 3,773,687 | 11/1973 | Borchert | 260/610 A |
| 3,778,382 | 12/1973 | Poenisch | 252/186 |

FOREIGN PATENTS OR APPLICATIONS

| | | | |
|---|---|---|---|
| 1,032,122 | 6/1966 | United Kingdom | 260/610 A |
| 1,232,710 | 5/1971 | United Kingdom | 260/610 A |

OTHER PUBLICATIONS

Noller et al., "A Relative Hazard Classification of Organic Peroxides," I and EC, Vol. 56, No. 12, Dec. 1964, pp. 18–27.
Armitage et al., "Safety Considerations in Industrial Use of Organic Peroxides," I and EC, Vol. 56, No. 12, Dec. 1964, pp. 28–32.

*Primary Examiner*—Leland A. Sebastian
*Assistant Examiner*—Irwin Gluck
*Attorney, Agent, or Firm*—John R. Ewbank

[57] ABSTRACT

A minor amount of a radical trap, that is, an organic compound readily reacting with an organic radical, when combined with a polyolefin having a metl index of from about 0.2 to about 10, can be associated with 70 per cent tertiary butyl hydroperoxide (containing about 30 per cent water). In the event of accidental conflagration of the combination, the combustion continues at a moderate rate, thereby avoiding the propensity toward troublesomely rapid burning of unmodified aqueous 70 per cent TBHP. Container liners should have a polyolefin thickness of 0.7 to 7 mm, the polyolefin containing such radical trap in a concentration of from about 0.1 to about 5 per cent, generally 0.2 to 2 per cent. If particulate polyolefin is used, the radical trap concentration should be from about 10 to about 100,000 parts per million parts of aqueous TBHP. A concentration of polyolefin particles from about 0.6 per cent to about 6 per cent by weight of the TBHP is suitable.

6 Claims, No Drawings

HAZARD REDUCTION FOR BULK SHIPMENT QUANTITIES OF AQUEOUS TERTIARY BUTYL HYDROPEROXIDE

RELATED APPLICATIONS

This is a continuation-in-part of our application Ser. No. 347,967, filed Apr. 4, 1973, now abandoned.

FIELD OF THE INVENTION

This invention relates to the inhibition of the troublesomely accelerated decomposition or rapid burning of an aqueous solution of an organic oxidant such as an organic hydroperoxide.

PRIOR ART

Heretofore the hazards of very rapid decomposition or combustion of organic oxidant materials has been sufficiently recognized that safety engineers have generally packaged such compositions in relatively small containers, such containers usually being polyethylene bottles. An aqueous solution containg about 30 percent by weight water and about 70 percent by weight of TBHP (tertiary butyl hydroperoxide) is a versatile material which has been used as a catalyst for various systems and which has also been used as an oxidant. Initially, customers were satisfied with shipment of TBHP-70 in pint bottles or other small containers. For a number of years, there has been a demand for shipment of 70 percent aqueous TBHP as a bulk shipment in tank cars. Being an organic oxidant, no bulk shipment could be made unless the freedom from hazards of troublesomely rapid decomposition or combustion was adequately established by appropriate proof. The knowledge that other peroxide compositions were dangerous under conflagration conditions was not only sufficient to restrict the packaging of 70 percent aqueous TBHP to small containers but also sufficient to guide interested parties to accept as permanent the classification of the significant hazards of the material.

Heretofore various oxidants have been shipped in combination with inhibitors adapted to minimize the danger of very rapid burning or decomposition, such hazard reductants being of the non-flammable, flame retardancy type adapted to retard the oxidizing propensities of the organic oxidant. Non-combustible solvents have also sometimes been employed to bring about the distribution of the organic oxidants throughout a sufficiently enlarged zone to inhibit unduly rapid decomposition or burning during any accident. Notwithstanding the abundance of research on fire retardants and the demand for better shipping containers for 70 percent aqueous TBHP, no satisfactory answer to the long-standing problem was developed.

Radical traps have heretofore been employed in inhibiting polymerization of monomers and in imparting a useful degree of resistance to sunlight in organic plastics.

SUMMARY OF THE INVENTION

In accordance with the present invention, the combustion hazards of an aqueous solution containing about 70 percent by weight TBHP (that is, tertiary butyl hydroperoxide) are significantly reduced by the use of a radical trap in a concentration from about 10 to about 100,000 parts of radical trap per million parts of TBHP, such radical trap being protected from precombustion inactivation by incorporation in a polyolefin. Examples of suitable radical traps include:
alkyl phenols
phenothiazines
substituted naphthyl amines
phenylene diamines
dibenzylamine
iminodibenzyl Other radical traps having effectiveness in inhibiting sunlight damage, polymerization, etc. are effective but outside the desired group of compounds.

The present invention also features a system comprising the combination of an aqueous solution containing about 70 percent by weight TBHP (that is, tertiary butyl hydroperoxide) and a hazard reducing quantity of a polyolefin having a melt index from about 0.2 to about 10. Such can be employed as a system inhibited to resist troublesomely rapid combustion (sometimes conveniently designated as rapid decomposition). In the event that such composition accidentally burns, it can burn to extinction without troublesomely rapid decomposition or combustion. Polyolefins are combustible, and it is surprising that the addition of such combustible component should function as a hazard reductant effectivee enough to overcome obstacles to bulk shipments of 70 percent TBHP. If the polyolefin is employed as a liner, its thickness should be within a range from 0.7 to 7 mm, or about 1/64 to about 1/4 inch. If particles of polyolefin are employed, they should constitute about 0.6 to 6 percent by weight of the composition.

DESCRIPTION OF PREFERRED EMBODIMENTS

The nature of the invention is further clarified by reference to a plurality of examples.

EXAMPLE 1

In a control test, a five-gallon steel pail was filled with about 4.5 gallons of aqueous TBHP-70 (tertiary butyl hydroperoxide containing 30 percent water) and placed on two 8-inch high cinderblocks for a combustion test. A lid having 4 holes of about ¼inch diameter was loosely positioned on top of the pail. Kindling wood, soaked with kerosene was placed beneath and around the pail, so that in the combustion, the flames approached several surfaces of the shipping pail. After the kindling had been ignited, the TBHP-70 took fire and the contents of the pail burned with moderate intensity. The combustion of the aqueous TBHP-70 appeared to advance satisfactory for about 20 minutes. However, just prior to the end of the burning of the aqueous TBHP-70, there was an accelerated decomposition (conveniently designated as a very rapid combustion) whereby the bottomm and sides of the pail were distorted, the lid was expelled from the pail, the fire was extinguished, and a muffled noise was heard. This type of rapid decomposition or burning near the end of the combustion of an organic oxidant is a type of hazard which had previously been observed for and was generally expected from concentrated aqueous solutions of organic oxidants. The restrictions which safety experts have imposed upon the transportation and storage of organic oxidant materials are attributable to such propensities toward troublesomely rapid decomposition or combustion.

In an example of the invention, several pieces of polyethylene, shaped as curved saddles and designed as contact surfaces in solvent extraction or distillation apparatus and having dimensions of about 3 inches long and about 1.8 inches wide were employed and floated on or near the top of surface of the TBHP-70. The saddles had a surface area of 227 square inches. The weight ratio of the polyethylene to the aqueous TBHP-70 was 0.0123 to 1; that is, the polyethylene constituted about 1.23 percent by weight of the TBHP-70. When the combination of the 4.5 gallons of aqueous TBHP-70 and 1.23 percent polyethylene was subjected to the standard combustion test using kerosene soaked kindling wood to heat the pail supported on 8-inch blocks, the material in the pail burned. There was no audible or visual indication of troublesomely rapid decomposition or combustion. Thus, it differed from the control in that the lid was not ejected and the sides of the pail were not distorted. The terminal portion of the burning of the organic oxidant was acceptable to safety standards because the presence of the polyethylene components so modified the total combustion that it could proceed smoothly until all of the combustible matter was consumed.

In another control, the 4.5 gallons of aqueous TBHP-70 were modified by the use of polyethylene saddles constituting 0.5 weight percent of the TBHP-70 and the standard combustion test was conducted. The TBHP burned for about 24 minutes at about which time the cover was blown from the pail by the intensity of the terminal stages of the combustion but there was no conspicuously loud explosive noise.

By a series of tests, it is established that when the polyethylene is in the form of particles, the concentration of the polyethylene should be at least 0.6 weight percent of the TBHP-70 and that little safety advantage is achieved by the use of more than 6.0 weight percent of the polyolefin. Such weight concentration limits are not relevant to lined containers, in which the thickness of the lining is the significant safety feature.

EXAMPLE 2

Polypropylene saddles, each saddle having a dimension of about 2 inches and marketed by the Norton Company as an "Intalox" brand of saddle are sometimes employed as packing in a distillation column. The addition of 30 saddles to 4.5 gallons of TBHP-70 represented about 1.8 percent by weight of the aqueous organic oxidant. In the standard combusion test, such proportions of polypropylene saddles are effective in maintaining the generally normal combustion of the organic material in the pail until all of such organic material was burned, thus avoiding the propensities of the unmodified TBHP to burn with troublesome rapidity.

EXAMPLE 3

A 5-gallon steel pail was modified by bonding a polyethylene liner thereto, the liner constituting 5.58 percent by weight of the 37 pounds (approximately 4.5 gallons) of TBHP-70. The combination was subjected to the previously described standard combustion test. Containers of organic oxidants must pass such standard test to meet the safety standards appropriate for transportation of merchandise. The contents of the polyethylene-lined pail burned for about 29 minutes with smooth combustion until the TBHP was completely burned in about 29 minutes. The lid was not ejected nor was there other evidence of troublesomely rapid decomposition or combustion. The polyethylene liner does effectively inhibit the propensities of the TBHP.

By a series of tests, it is established that the thickness of a polyolefin (e.g., polyethylene, polypropylene, etc.) liner should be from about 0.7 to about 7 mm. (about 1/64 to about ¼ inch) and that the melt index of the polyolefin must be within the range from 0.2 to 10 as measured by ASTM 1238 Condition E procedure. It is important that the polyolefin be free from metallic contaminanta (e.g., residues from catalysts) scrap, and/or pigments which might alter its modifying role.

In a control procedure a sample of polyethylene having a melt index of 0.1 (that is, half of the minimum requirement of the present invention) is subjected to a molding operation in an effort to provide a liner for a five-gallon bucket. Difficulties are encountered in the adhesion of the liner in the molding and in the cooling of the molded liner from molding temperature. The thus defined pail is subjected to the standard combustion test, during which the lid is expelled and a noise is heard indicative of troublesomely rapid combustion. Such adverse result is possibly attributable to a propensity of the difficulty meltable polyethylene to burn only at the interface of liquid and air instead of predominantly melting before combustion.

In a control procedure, a sample of polypropylene having a melt index of 15 is employed in the form of short hollow tubes (such as is used as packing in liquid vapor contact towers) dispersed in aqueous 70 percent tertiary butyl hydroperoxide, the polypropylene constituting 0.7 percent by weight of the composition. In the combustion test, the lid is expelled and a noise indicates troublesomely rapid decomposition or burning. The polypropylene has a sufficiently low melting point that substantially all of the polypropylene is melted and burned during the early portions of the test, leaving no polypropylene for modifying the terminal phases of the combustion.

By a series of tests, it is established that the melt index for the polyolefin must be within a range from 0.2 to 10.

EXAMPLE 4

In a control, a 55-gallon steel drum filled with 70 percent aqueous TBHP was subjected to the standard combustion test, and the steel drum was destroyed by the rapidity of the terminal stages of the burning.

A commercially available drum having a polyethylene liner was employed in the same test and shown to be a safe container. The flames continued for 50 minutes without troublesomely rapid burning. The 2SL polyethylene liner had a melt index of 2.6 and a density within a range from 0.910 to 0.925 and was about 3/16 inch thick.

As an example of the present invention, a semitrailer having a 2000 gallon steel tank is lined with polyethylene having a thickness of 5 mm., a density of about 0.92, and a melt index of about 2.0. The tank is partially filled with TBHP-70 and ignited. The combustion advances smoothly, and the composition burns without troublesomely rapid decomposition or combustion, by reason of the presence of the polyethylene liner in the tank.

With the aid of retrospect, it is believed that the combustion of the polyethylene or other thermoplastic polyolefin is initiated and advances concurrently with the combustion of the TBHP and that during the final stages of the combustion, when the oxidant concentration is high and the temperature is high, tending to promote troublesomely rapid decomposition or combustion, the combustion of the plastic consumes the oxidant at a rate sufficient to avoid the developement of such troublesomely rapid burning rates.

EXAMPLE 5

2-methyl,4,6-di-tertiarybutyl phenol (conveniently abbreviated as MDTBP) is a useful inhibitor for reducing the rate of reactions involving a free radical mechansim. Discoloration of organic liquids exposed to sunlight, polymerization of monomers, and thermal activation of hexaarylyl plumbanes are inhibited by MDTBP. Particles of MDTBP are encapsulated in polypropylene to provide a flowable powder of spheroids functioning as a microencapsulated form of MDTBP, the polypropylene skin constituting about 25 percent of the weight of each spheroid. In a series of tests, in each of which a bucket containing about 35 pounds of TBHP is modified by the addition of a controlled amount of spheroids of encapsulated MDTBP and subjected to the standard combustion test, it is shown that the concentration of MDTPBP desirably should be between about 10 and about 100,000 parts of MDTPB per 1,000,000 parts of aqueous TBHP. Concentrations greater than 10 ppm but less than 10,000 ppm are preferred.

By using 1,000 ppm, the microencapsulated phenol achieves a sufficiently reliable reduction of hazard during combustion to offer an attractive combination of advantages. The microencapsulated phenol is more costly per pound than polyolefin, but by using a smaller concentration of microencapsulated phenol, adequate reduction of hazard is attainable at a competitive price. For shipments involving costly freight costs and involving single usage of the modifier, encapsulated phenol spheroids offer an economic advantage even when more costly when comparing merely the expense of formulation.

In a series of tests of microencapsulated radical traps, it is shown that 1,000 parts of radical trap per 1,000,000 parts of aqueous TBHP, it is shown that phenothiazines such as 4,6 dimethylphenothiazine, substituted naphthyl amines such as 3–4 dimethylalphanaphthyl amine, phenylenediamines such as 2,4 diaminotoluene, dibenzyl amines such as bis(s-$ClC_6H_4CH_2)_2NH$, and iminodibenzyls such as p $Me_2Nc_6H_4C_2H_4C_6H_4NMe_2$, are effective agents for reducing the hazard in combustion of TBHP.

Another phenol found to be satisfactory is DTBMP or 2,6,di-t-butyl,-4-methyl phenol. The trademark "IONOL" identifies one brand of such DTBMB.

Polyolefin manufacturers regularly employ controlled amounts of radical traps in all molded products. For example, some polyethylene saddles contain about 0.25 weight percent of IONOL brand of DTBMP (2,6 di-t-butyl-4-methyl phenol). Low density polyethylene having a melt index of 1.1 and containing about 0.25 weight percent IONOL brand of DTBMP is manufactured as a flexible sheet about 4 mm. thick. The sheet is cut to provide about 194 g. of polyethylene as 18 rectangular ribbons about 51 mm. by 25 mm. These ribbons are employed in the 35 pound of aqueous TBHP in the standard combustion test and found to be effective in preventing an excessive rate of terminal decomposition. Such test established the usefulness of 35 ppm of IONOL as a combustion modification agent.

EXAMPLE 6

Low density polyethylene having a melt index of 2.1 and containing 0.15 percent IONOL was fabricated into saddles suitable as packing for treatment towers. Six saddles (188 g.) were employed in the standard combustion test. The concentration of IONOL in aqueous TBHP was about 18 ppm and was sufficient to avoid the troublesomely excessive decomposition.

The need for the modification of the decomposition is only for the final minutes of the burning, and whatever modifier is employed must be preserved in a form having appropriate effectiveness after most of the TBHP has burned. The polyolefin might be interpreted as the significant modifier. The radical trap might be interpreted as the significant modifier. Regardless of theoretical interpretations of the results, the facts show that troubles are avoided by the use of polyolefin containing radical trap materials, thus providing a basis for claiming the process featuring the polyolefin as well as the process featuring the radical trap.

Various modifications of the invention are possible without departing from the scope of the appended claims.

We claim:
1. The method of inhibiting troublesomely rapid combustion of a body of aqueous tertiary butyl hydroperoxide suitable for bulk shipment in a tank which method consists essentially of associating bulk-shipment sized body of aqueous tertiary butyl hydroperoxide consisting essentially of 30 percent water and 70 percent tertiary butyl hydroperoxide with a minor amount of polyolefin having a melt index within the range from 0.2 to 10, said polyolefin being selected from the group consisting of polyethylene and polypropylene, said method providing a metal container having said minor amount of polyolefin present as a liner having a thickness within the range from about 0.7 to 7 mm., and the aqueous tertiary butyl hydroperoxide being stored within such lined container.

2. The method of inhibiting troublesomely rapid combustion of a body of aqueous tertiary butyl hydroperoxide suitable for bulk shipment which method consists essentially of associating bulk-shipment sized body of aqueous tertiary butyl hydroperoxide consisting essentially of 30 percent water and 70 percent tertiary butyl hydroperoxide with a minor amount of polyolefin having a melt index within the range from 0.2 to 10, said polyolefin being selected from the group consisting of polyethylene and polypropylene, said method providing particles of polyolefin admixed with said aqueous tertiary butyl hydroperoxide stored in a metal container, said polyolefin particles constituting from 0.6 to 6.0 weight percent of the composition in such container.

3. The method of inhibiting troublesomely rapid decomposition during the terminal stages of combustion of a body of aqueous tertiary butyl hydroperoxide suitable for bulk shipment in a tank which method consists essentially of associating bulk-shipment sized body of aqueous tertiary butyl hydroperoxide consisting essentially of 30 percent water and 70 per cent tertiary butyl hydroperoxide with a minor amount of polyolefin having a melt index within the range from 0.2 to 10, said polyolefin being selected from the group consisting of polyethylene and polypropylene, said method providing a metal container having said minor amount of polyolefin present as a liner having a thickness within the range from about 0.7 to 7 mm., and the aqueous tertiary butyl hydroperoxide being stored within such lined container, said polyolefin containing a hazard reducing quantity of radical trap of the group consisting of alkyl phenols, phenothiazines, substitute naphthyl amines, phenylene diamines, dibenzyl amine, and iminodibenzyl, the quantity of said radical trap constituting from about 10 to about 100,000 parts per million parts of aqueous tertiary butyl hydroperoxide, whereby such combination burns safely to extinction without troublesomely rapid decomposition.

4. The method of inhibiting troublesomely rapid combustion of a body of aqueous tertiary butyl hydroperoxide suitable for bulk shipment which method consists essentially of associating bulk-shipment sized body of aqueous tertiary butyl hydroperoxide consisting essentially of 30 percent water and 70 percent tertiary butyl hydroperoxide with a minor amount of polyolefin having a melt index within the range from 0.2 to 10, said polyolefin being selected from the group consisting of polyethylene and polypropylene, said method providing particles of polyolefin admixed with said aqueous tertiary butyl hydroperoxide stored in a metal container, said polyolefin particles containing a minor amount of radical trap selected from the group consisting of alkyl phenols, phenothiazines, substituted naphthyl amines, phenylene diamines, dibenzyl amine, and iminodibenzyl, the quantity of said radical trap constituting from about 10 to about 100,000 parts per million parts of aqueous tertiary butyl hydroperoxide, whereby such combination burns safely to extinction without troublesomely rapid decomposition.

5. The method of claim 4 in which said polyolefin particles constitute from 0.6 to 6.0 weight percent of the composition in such container.

6. The method of claim 5 in which the radical trap is an alkyl phenol in a concentration range less than 10,000 ppm.

* * * * *